United States Patent
Ritzdorf et al.

(10) Patent No.: US 10,335,377 B2
(45) Date of Patent: Jul. 2, 2019

(54) OVER-PATCH HAVING IMPROVED COMPATIBILITY AND A LONG ADHESION DURATION AND METHOD FOR PRODUCING SAID OVER-PATCH

(71) Applicant: LTS Lohmann Therapie-Systeme AG, Andernach (DE)

(72) Inventors: Gerhard Ritzdorf, Hammerstein (DE); Thomas Hille, Neuwied (DE); Petra Botzem, Andernach (DE); Gabriel Wauer, Ahrweiler (DE); Marlene Fuhrmann, Kail (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 15/126,701

(22) PCT Filed: Mar. 16, 2015

(86) PCT No.: PCT/EP2015/000579
§ 371 (c)(1),
(2) Date: Sep. 16, 2016

(87) PCT Pub. No.: WO2015/139830
PCT Pub. Date: Sep. 24, 2015

(65) Prior Publication Data
US 2017/0087098 A1    Mar. 30, 2017

(30) Foreign Application Priority Data
Mar. 19, 2014 (EP) ..................... 14160657

(51) Int. Cl.
*A61M 25/02*  (2006.01)
*A61K 9/70*   (2006.01)
*A61L 15/34*  (2006.01)
*A61L 15/58*  (2006.01)

(52) U.S. Cl.
CPC ........... *A61K 9/7061* (2013.01); *A61L 15/34* (2013.01); *A61L 15/58* (2013.01)

(58) Field of Classification Search
CPC ............... A61K 9/7084; A61M 25/02; A61M 2025/0266
See application file for complete search history.

(56) References Cited

U.S. PATENT DOCUMENTS

| | | | | |
|---|---|---|---|---|
| 5,236,421 A | * | 8/1993 | Becher | A61M 25/02 602/54 |
| 5,273,757 A | * | 12/1993 | Jaeger | G01N 33/521 424/448 |
| 5,670,164 A | * | 9/1997 | Meconi | A61K 9/7076 424/448 |
| 6,315,854 B1 | * | 11/2001 | Anhauser | A61K 9/7061 156/250 |
| 6,814,976 B1 | * | 11/2004 | Hille | A61K 9/7061 424/443 |
| 7,914,645 B2 | * | 3/2011 | Schalau, II | A61K 9/7007 156/329 |
| 8,323,684 B2 | * | 12/2012 | Bracht | A61K 9/7061 424/443 |
| 2009/0130190 A1 | | 5/2009 | Breitenbach et al. | |
| 2011/0144470 A1 | | 6/2011 | Mazar et al. | |

FOREIGN PATENT DOCUMENTS

| | | | |
|---|---|---|---|
| DE | 10 2004 038 285 A1 | 4/2006 | |
| DE | 10 2006 054 731 A1 | 5/2008 | |
| EP | 0 247 571 A1 | 12/1987 | |
| EP | 0380989 A2 | * 8/1990 | ........... A61K 9/0014 |
| EP | 1 992 363 A1 | 11/2008 | |
| EP | 2 759 294 A1 | 7/2014 | |
| WO | WO 1987/07164 A1 | 12/1987 | |
| WO | WO 2002/38136 A2 | 5/2002 | |
| WO | WO 2006/036899 A2 | 4/2006 | |
| WO | 2009/009649 A1 | 1/2009 | |

OTHER PUBLICATIONS

Tan, H.S., Pfister, W.R., 1999. Pressure-sensitive adhesives for transdermal drug delivery systems. Pharm. Sci. Technol. Today 2, 60-69.*
Selection Guide for Hercules Hydrocarbon Resins, 2nd Edition. Hercules BV (Netherlands). Oct. 1993.*
"Heilmann, Klaus: Therapeutische Systeme Konzept und Realisation programmierter Arzneiverabreichung" [Therapeutic systems Concept and Realization of Programmed Pharmaceutical Adminstration], 4th edition, Ferdinand Enke Verlag Stuttgart, 1984, pp. 26-37.
Roberts, Wendy E., *Journal of Drugs in Dermatology*, May 2008, vol. 7, Issue 5, pp. 452-456.
Roberts, Wendy E., "Skin Type Classification Systems Old and New," *Dermatol. Clin.*, Oct. 2009, vol. 27, Issue 4, pp. 529-533.
International Preliminary Report on Patentatibility of International Application No. PCT/EP2015/000579.

* cited by examiner

*Primary Examiner* — Bethany P Barham
*Assistant Examiner* — Peter Anthopolos
(74) *Attorney, Agent, or Firm* — ProPat, L.L.C.; Vinisha Joshi

(57) ABSTRACT

The invention relates to a medical product for a fastening duration of at least 7 days having good skin compatibility. The medical product includes a central adhesive compartment (3) and an over-patch. The over-patch is free of active ingredients and is formed from a water-vapor-permeable back layer (1) and an adhesive polymer layer (2) that is free of active ingredients. The invention further relates to a method for the production of the foregoing medical product, and to kits of parts containing laminates of layers 1 and 2.

15 Claims, 1 Drawing Sheet

OVER-PATCH HAVING IMPROVED COMPATIBILITY AND A LONG ADHESION DURATION AND METHOD FOR PRODUCING SAID OVER-PATCH

CROSS-REFERENCE TO RELATED APPLICATIONS

This application is being filed under 35 U.S.C. § 371 as a National Stage Application of pending International Application No. PCT/EP2015/000579 tiled Mar. 16, 2015, which claims priority to the following parent application: European Patent Application No. 14160657.4 tiled Mar. 19, 2014. Both International Application No. PCT/EP2015/000579 and European Patent Application No. 14160657.4 are hereby incorporated by reference herein in their entirety.

FIELD OF THE INVENTION

The invention relates to medical products having good skin compatibility. The medical products comprise a central adhesive compartment and an over-patch.

BACKGROUND OF THE INVENTION

The present invention relates to medical products which are worn on the skin and fastened by an overplaster. These products may be transdermal therapeutic systems (TTS) which, besides the part containing active ingredient, additionally an active-ingredient-free overplaster, which has a specific construction, but also diagnostic agents or cannulas which are fixed by a piaster dressing. As is known, TTS are medicinal products in patch form which are adhered to the skin and are required to deliver at least one active ingredient over the entire administration time. It is obvious that, these medical properties must adhere well, since otherwise there can be no delivery of active ingredient to the skin, the diagnostic agent does not work reliably, or the cannula slips. At the same time, instances of skin irritation must be prevented, meaning that the inherent tack of the TTS, diagnostic agent or cannula fixing plaster may not be higher than is absolutely necessary.

Adhesive bonding, as is known, refers to the joining of two surfaces by an adhesive that connects the surfaces to one another through adhesion and cohesion. The adhesive here has to wet the respective surfaces. It follows from this that effective tack is governed not only by the adhesive but also by the nature of the surfaces. But different people, particularly with progressing age, have skins with different surfaces, with the individual skin types varying in their sensitivity of reaction to skin irritations. Although this requirement is familiar to the art, there are still no medical products which address this issue.

EP 1 992 363 discloses a transdermal patch having a backing laver and a pressure-sensitively adhering layer, which in turn comprises an active ingredient reservoir layer and a layer which adheres on the skin. The active ingredient reservoir layer comprises a pressure-sensitive acrylate adhesive, while the layer that adheres to the skin comprises a styrene-isoprene-styrene block copolymer.

DE 10 2004 038 285 A1 discloses a patch system for the release of essential oils via the ambient air or transdermally without irritation to the mucosae or the skin. The patch system comprises a polymer matrix in which at least one essential oil is homogeneously distributed, a support layer, and a removable protective layer. Additionally, there may be a blockage layer impermeable to essential oils, a permeation-controlling membrane or a pressure-sensitive adhesive layer present.

Subject-matter of DE 10 2006 054 731 A1 is a transdermal therapeutic system for administering, buprenorphine. This system comprises a backing layer impermeable for the active ingredient, a matrix layer based upon polysiloxane or polyisobutylene, and comprising as well as buprenorphine at least one carboxylic acid, and a detachable protective layer.

Disclosed in EP 2 759 294 A1 is a patch for the transdermal administration of fentanyl or a fentanyl homolog. The patch comprises a backing layer, a barrier layer, a pressure-sensitively adhering active ingredient layer, and a removable protective layer (release layer). The active-ingredient-containing layer contains fentanyl or a fentanyl homolog, an agent for improving the permeation of the fentanyl or the fentanyl homolog, and an acrylate adhesive. The acrylate adhesive is either a nonfunctional polyacrylate adhesive or a polyacrylate adhesive which contains carboxyl groups.

Plasters of polyacrylates which can be utilized over a wear time of up to at least 7 days, are known from US 2009/0130190 A1, for example. Particularly when worn for a long time, plasters of this kind load generally, on redetachment, to significant pain for the skin affected, and to increased visible residues on the skin. A further factor is the commonplace use of basis weights of more than 80 g/m$^2$, with the disadvantage of higher residual monomer contents in the plaster as a whole. The origin of this is that for overplasters, which are designed for at least 7 days, it is common for acidic polyacryate adhesives (monomers have free acid functions) to be used, without additions such as neutral oils, and they therefore enter into a very strong bond to the skin.

In the case of silicone adhesives containing active ingredient, amine-resistant silicone adhesives are often utilized as skin contact layers. These adhesives often have the disadvantage that on account of their amine resistance, they exhibit relatively low bonding to the skin, since all of the terminal silanol groups are capped by methyl groups. With the commonplace silicone adhesives, therefore, it is often very difficult to attain a wear time of at least 7 days or more. Additionally, amine-resistant polysiloxane adhesives have lower water vapor transmissibility figures than is the case for non-amine-resistant versions of the polysiloxane adhesives, and so the occlusion effect is smaller with these adhesives. This disadvantage can be compensated if utilizing an overplaster which adheres with high compatibility to the skin for at least 7 days. As a further aspect, a single-sided siliconized film (e.g. 19 or 23 μm PET film with single-side siliconization) is often utilized as a backing layer in the case of silicone piasters containing active ingredient. Here, the deleterious effect occurs that it also has silicone residues on the nonsiliconized side, since the rolls are wound into themselves, causing the nonsiliconized side to make contact with the siliconized side. The adhesion relative to the active-ingredient-containing silicone adhesive layer is therefore good, but is lower than that of an overplaster based on acrylate adhesives. Consequently there may be instances of premature detachment (and/or poor adhesion) between overplaster and active ingredient-containing matrix with a release layer composed of single-sidedly siliconized film (or backing layer). This disadvantage can be compensated by an active-ingredient-free overplaster which is based on non-amine-resistant silicone adhesives.

SUMMARY OF ADVANTAGEOUS EMBODIMENTS OF THE INVENTION

It was an object of the present invention, therefore, to provide an active-ingredient-free overplaster which does not have the disadvantages of the prior art or has them only to a far smaller extent.

This object is achieved by medical products having a central compartment and an active-ingredient-free overplaster which overhangs the central compartment on all sides, since this construction takes account of the requirements of standardized production processes. allowing the essential part to be fabricated in large batches, while the variations necessary because of the different skin types become possible through different overplasters. For the adhering part in direct skin contact, preference is given to silicone adhesives featuring enhanced water vapor permeability and consequent lower occlusion effect, or to polyacrylate adhesives with addition of neutral oil. The silicone adhesive may further comprise silicone oils as tackifiers. For improved skin compatibility, the polyacrylate adhesive comprises a neutral oil, in order to ameliorate the bonding performance particularly on redetachment.

DETAILED DESCRIPTION OF ADVANTAGEOUS EMBODIMENTS OF THE INVENTION

Figure 1:
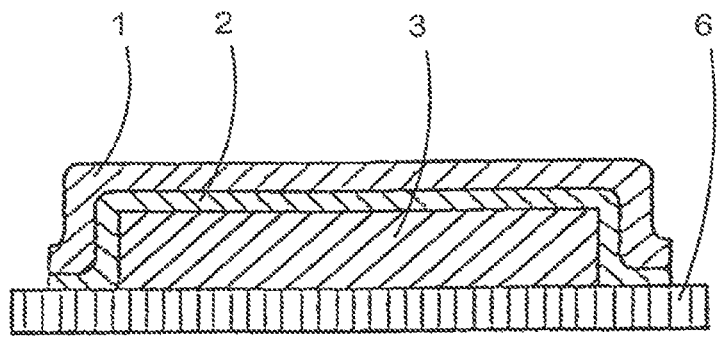
FIG. 1 is a schematic cross-sectional view of an exemplary inventive medical product.

As backing layer 1, an elastic fabric permeable for water vapor can be utilized, in order to give the plaster a certain flexibility. This layer is preferably made of polyester fabric and may be given appropriately different coloring for more effective differentiation between the types of overplaster. Used with preference is a bidirectionally elastic polyester fabric which is stretchable in warp and weft directions, more particularly a polyethylene terephthalate fabric. The stretchability of this fabric is ≥35%, preferably ≥45%, more particularly about 50% in lengthwise direction and ≥25%, preferably ≥35%, in transverse direction, measured according to DIN 61632. The basis weight is ≥100 g/m$^2$, preferably ≥120 g/m$^2$, more particularly about 130 g/m$^2$. Karl Otto Braun GmbH & Co. KG (KOB) is one manufacturer of such fabrics.

A further constituent of the invention is the utilization of very low coating weights. Surprisingly it has emerged that as a result of this, the amount of residual monomers which may be present in polyacrylate adhesives after drying can be kept smaller, with the plaster nevertheless remaining adhering for 7 days. The silicone adhesive variant displays the advantage that in that case there are no residual monomers present at all. As further alternative polymers for the active-ingredient-free overplaster, it is also possible for polyisobutylene/butylene or styrene-isoprene (alternatively: butadiene)-styrene block copolymers to be utilized. These copolymers can often be employed in combination for the purpose of increasing the bonding performance with hydrogenated hydrocarbon resins and/or oils, liquid paraffin for example. The resins and oils are preferably used in a highly purified state, thereby improving the skin compatibility.

This overplaster serves preferably for the fixing of active-ingredient-containing matrix plasters consisting of an active-ingredient-containing layer of adhesive, in which amine-resistant polysiloxane adhesives, polyacrylate adhesives or polyisobutylene adhesives find application as adhesive. This layer of adhesive is in direct skin contact. As a separating layer relative to the active-ingredient-free overplaster, a PET film barrier layer is employed, which in the case of silicone adhesive systems is usually single-sidedly siliconized. The overplaster is applied with an overlapping edge, and so the overlapping, active-ingredient-free edge of the overplaster ensures fixing over a wear period of at least 7 days.

The present invention therefore relates to a medical product consisting of a central compartment (3) and an active-ingredient-free overplaster composed of
  a) a water vapor-permeable backing layer (1) and
  b) a pressure-sensitively adhering, active-ingredient-free polymer layer (2) which is not amine-resistant and which comprises highly water vapor-permeable polysiloxanes, polyacrylates without or only with few free acid groups, polyisobutylenes, polybutylenes, styrene-isoprene-styrene block copolymers or styrene-butadiene-styrene block copolymers or the homo- and/or copolymers thereof, wherein the compartment 3 is pressure-sensitively adhering and has direct skin contact after removal of the redetachable protective layer (6), which is characterized in that the composition of the layer 2 is selected as a function of the requirements of the patient's specific skin type in such a way that the medical product can be utilized for a fixing time of at least 7 days (wear time without complete detachment of the plaster of at least 7 days on intact human skin) while meeting the requirements for good skin compatibility.

This product is preferably a transdermal therapeutic system (TTS) wherein the compartment 3 consists of
  c) at least one pressure-sensitively adhering, active-ingredient-containing polymer layer (5) which has direct skin contact after removal of the redetachable protective layer (6), and
  d) a separating layer (4), preferably of polyester, which covers the layer 5.

The medical product of the invention may also be a diagnostic agent, in which case the diagnosis apparatus is located in the compartment 3; or it may be a cannula fixing plaster, in which case the cannula is located in the compartment 3. US 2011/144470 A1 discloses diagnosis apparatus adhered to the skin. Fixing systems for the attachment of cannulas on the skin are described for example in WO 87/07164 A1.

The preferred TTS are drug forms for application to the skin, with the appearance of traditional plasters, which comprise drugs for delivery via the skin. A TTS may contain one or mere drugs, which are delivered continuously at a predetermined rate over a specified period of time to a stipulated site of application ("Heilmann, Klaus: Therapeutische Systeme Konzept und Realisation programmierter Arzneiverabreichung" [Therapeutic systems Concept and Realization of Programmed Pharmaceutical Administration], 4th edition, Ferdinand Enke Verlag Stuttgart, 1984, p. 26).

The active-ingredient-containing layer of pressure-sensitive adhesive in the TTS consists of a polymer matrix with a base polymer and optionally the customary additions. Suitable polymers are silicones, rubber, rubberlike synthetic homo-, co- or block polymers, polyacrylic esters and their copolymers, and esters of hydrogenated rosin. Suitable in principle are all polymers which are used in the production of pressure-sensitive adhesives and are physiologically unobjectionable. Suitable examples include those which consist as block copolymers on the basis of styrene and 1,3-dienes, polyisobutylenes, or polymers and copolymers of acrylate and/or methacrylate. Of the block copolymers based on styrene and 1,3-dienes, linear styrene-isoprene-styrene block copolymers, for example, are used.

Examples of preferred acrylate-based polymers are acrylate copolymers of 2-ethylhexyl acrylate, vinyl acetate and acrylic acid, with or without titanium chelate esters. Esters of hydrogenated rosin that are used are preferably its methyl esters and glycerol esters.

The nature of the tackifiers and plasticizers which are possible as additions is dependent on the polymer used. The physiologically unobjectionable substances contemplated are known. The inherent tack of the layer of pressure-sensitive adhesive must ensure lasting contact to the skin. The layer may be applied in a hotmelt process, as a solution or as a pressure-sensitive dispersion-based adhesive to the backing layer.

Active ingredients used are substances which when applied to the skin, without or with absorption mediators, bring about a local or systemic effect.

Ingredients with local effect are, for example, antiperspirants, fungicides, bactericides, and bacteriostatics.

Examples of ingredients with systemic effect are antibiotics, hormones, antipyretics, antidiabetics, coronary dilators, cardioactive glycides, spasmolytics, antihypertensives, psychopharmaceuticals, migraine agents, corticoids, analgesics, anticontraceptives, antirheumatics, anticholinergics, sympatholytics, sympathomimetics, vasodilators, anticoagulants and antiarrhythmics.

Possible additions dependent on the polymer employed and on the active ingredient are plasticizers, tackifiers, stabilizers, carriers, diffusion- and penetration-regulating additions, or fillers. The physiologically unobjectionable substances contemplated are known.

The layer 2 may contain 0 to 5% (w/w) of a neutral oil, based on the dry weight of this layer, as compatibilizer. Layer 2 may also contain 0.5 to 5% (w/w) of dexpanthenol, based on the dry weight of this layer.

Layer 2 may also comprise a non-amine-resistant polysiloxane polymers in which, after the polycondensation of the resin fraction and of the polydimethylsiloxanol groups, the remaining silanol groups still free have not been capped by methyl groups, to which 0 to 4% (w/w) of silicone oil are added, based on the dry weight of this layer.

Layer 2 may further comprise polyacrylates or vinyl-acrylate copolymers which have an acid number of less than 1.

Layer 2, finally, may also comprise styrene-isoprene-styrene block copolymers or styrene-butadiene-styrene block copolymers in combination with hydrogenated hydrocarbon resins and/or oils such as liquid paraffin.

In particular, the preferred TTS has the stated layers in each case once, and it consists preferably of the stated layers. The two stated pressure-sensitively adhering layers may be alike or different in terms of their polymer composition and/or thickness. The pressure-sensitively adhering polymer layer for application to the skin is preferably provided additionally with a protective layer composed, in the case of acrylate and of polyisobutylene adhesives, of, for example, siliconized paper or siliconized film (e.g., PET film). In the case of silicone adhesives, a fluoropolymer-coated PET protective layer is employed. The individual plasters are packaged in a customary way, as for example in a four-edge sealed pouch of composite packaging material made of polyacrylonitrile, aluminum foil, and paper.

The pressure-sensitively adhering and skin-friendly polymer layer 2 which is in skin contact comprises preferably non-amine-resistant polysiloxanes, polyacrylates or polyisobutylenes. Preferably this polymer layer comprises or consists of one or more vinyl acetate-acrylate copolymers whose monomers have no or few free acid groups and therefore have an acid number of less than 1. More preferably this layer consists of a non-amine-resistant polysiloxane that may include small amounts of silicone oil for the purpose of increasing the tack.

It is a particular feature of the overplaster of the invention that the pressure-sensitively adhering and skin-friendly polymer layer 2 in skin contact can comprise non-amine-resistant polysiloxanes with or without silicone oil for increasing the tack, in very small quantities, and in one preferred embodiment also comprises said polysiloxanes.

It is a further particular feature of the overplaster of the invention that when a polyacrylate is utilized, this polyacrylate consists of the group of the vinyl acetate-acrylate copolymers, and after polymerization there are no or few free acid groups present, and additionally a neutral oil is utilized for increasing the skin compatibility, particularly on redetachment.

The impermeable separating layer (4) between active-ingredient-containing layer and overplaster may consist of various polymers. Preferred here are polyesters and, of these, especially polyethylene terephthalate. The layer 4 is employed as soon as there is an active-ingredient-delivering unit to be separated from the active-ingredient-free overplaster unit.

Well-adhering polymers are, for example, polyacrylates. Adhering particularly well to the skin are polyacrylates which have been prepared using free acrylic acid. However, these polyacrylates lead to instances of skin irritation and marked pain on redetachment. In wearing trials, polyacrylates were utilized without free acrylic acid, in order to verify a wear time in conjunction with high skin compatibility. These trials, as part of $2^2$-factor trial plans, were successful. It is therefore possible with preference to use polymers having acid numbers of <1.

The same observations are also applicable in principle to polysiloxanes, with acid monomers being absent from these polymers on account of their different chemical construction. Therefore they adhere reliably over a time of at least 7 days only when they are prepared using "standard PSA", non-amine-resistant polysiloxane adhesives, in order to have sufficient hydrophilic structures with increased binding affinity to the skin.

Dexpanthenol, which may likewise be employed in the overplaster, is converted within the body into pantothenic acid. Pantothenic acid is a vitamin from the group of the B vitamins (vitamin B5). Pantothenic acid is a constituent of coenzyme A and hence plays a key part in skin metabolism. On account of its hydrophilicity, dexpanthenol in the context of this invention is not employed with the apolar polymers such as polyisobutylenes and polysiloxanes, since it would have to be incorporated by means of a hydrophilic solvent, as for example ethanol or other alcohols (dexpanthenol is virtually insoluble in very apolar solvents, of the kind employed for polyisobutylene/polybutylene and polysiloxane adhesives, e.g. n-heptane). Production would require a kind of emulsion, with known disadvantages such as phase separation, coalescence, etc. In the context of use in polyacrylates, incorporation of dexpanthenol was easy, since these polymers are employed in polar solvents such as in mixtures of ethyl acetate and ethanol. At relatively high concentrations, use in the case of polyacrylates led to significant residues on the skin after wearing, since it lowered the cohesion. Additionally, at concentrations of, for example, 5% [w/w], it lowers the wear time to below 7 days, on account of its plasticizer properties.

It has emerged that a TTS with an active-ingredient-free overplaster in accordance with the invention exhibits a significantly lower propensity toward crystallization of the active ingredient/ingredients in the pressure-sensitively adhering, active-ingredient-containing polymer layer 5. Moreover, it has much less of a propensity toward cold flow. This means that the TTS more rarely remains sticking to the surface of the packaging, and can therefore be removed more easily from the sealed edge pouch.

The invention therefore also relates to the use of an active-ingredient-free overplaster for preventing the crystallization of the active ingredient/ingredients in the active-ingredient-containing polymer layer 5 of a TTS, and to the use of an active-ingredient-free overplaster for reducing the cold flew in a TTS.

The invention also relates to methods for producing the medical product of the invention, which is characterized in that the compartment 3 is produced conventionally and its skin-side adhesive face is lined with a redetachable protective layer (6) which protrudes on all sides by at least 4 mm, the patient's skin type is classified by the method, for example, of W. E. Roberts, and then, with the aid of this classification, a selection is made, from a group encompassing non-amine-resistant, highly water vapor-permeable polysiloxanes, polyacrylates without or only with few free acid groups, polyisobutylenes, polybutylenes, styrene-isoprene-styrene block copolymers or styrene-butadiene-styrene block copolymers or their homo- and/or copolymers, of those polymers—and, optionally, from the additions claimed in the preceding claims, a selection is made of those additions—which are necessary in order for the medical product to be able to be utilized for a fixing time of at least 7 days while meeting the requirements for good skin compatibility, coating material is produced therefrom and is coated onto an intermediate carrier and dried, the backing layer 1 is laminated onto the resulting laminate of layer 2 and intermediate carrier, and from this laminate an overplaster is punched out in a size and shape which overhangs the compartment 3 on all sides by at least 4 mm, and the resulting overplaster, finally, after removal of the intermediate carrier, is adhered to the side of the compartment 3 that is facing away from the skin-side adhesive face, in such a way that it overhangs this compartment on all sides by at least 4 mm.

The W.E. Robert Skin Type Classification System was introduced in recent times in order to allow the classification of skin type in the case, for example, of cosmetic treatments (see, e.g., Roberts, J. Drugs Dermatol. 2008 May; 7(5): 452-456 and Robert, Dermatol. Clin. 2003 Oct; 27(4): 529-533). It is a four-part system which not only determines the properties of the skin type but also provides information on the prognosis of the skin reactions.

The invention also relates to a kit-of-parts comprising a compartment 3 which is provided on the skin-side adhesive face with a redetachable protective layer (6), the compartment 3 being as defined in any of claims 1 to 4, and at least one active-ingredient-free overplaster which is laminated to an intermediate carrier and is composed of
a) a water vapor-permeable backing layer (1) and
b) a pressure-sensitively adhering, active-ingredient-free polymer layer (2) comprising non-amine-resistant, highly water vapor-permeable polysiloxanes, polyacrylates without or only with few free acid groups, polyisobutylenes, polybutylenes, styrene-isoprene-styrene block copolymers or styrene-butadiene-styrene block copolymers or the homo- and/or copolymers thereof. The kit preferably comprises at least two active-ingredient-free overplasters as defined and laminated onto an intermediate carrier, said overplasters differing in terms of the composition of the layer 2, their size and/or their shape. With this preferred embodiment, the user obtains a "construction kit" allowing them to combine the compartment 3, manufactured in a standardized process and meeting strict pharmaceutical stipulations, with a suitable overplaster, allowing the medical product to be used in accordance with the requirements for a fixing time of at least 7 days and at the same time meeting the requirements for good skin compatibility.

The invention further relates to a kit-of-parts comprising at least two active-ingredient-free overplasters laminated onto an intermediate carrier and composed of
a) a water vapor-permeable backing layer (1) and
b) a pressure-sensitively adhering, active-ingredient-free polymer layer (2) comprising non-amine-resistant, highly water vapor-permeable polysiloxanes, polyacrylates without or only with few free acid groups, polyisobutylenes, polybutylenes, styrene-isoprene-styrene block copolymers or styrene-butadiene-styrene block copolymers or the homo- and/or copolymers thereof, where the overplasters differ in terms of the composition of the layer 2, their size and/or their shape.

With this kit as well, the user obtains a "construction kit" allowing them to combine the compartment 3, manufactured in a standardized process and meeting strict pharmaceutical stipulations, with a suitable overplaster, allowing the medical product to be utilized in accordance with the requirements for a fixing time of at least 7 days while meeting the requirements for good skin compatibility.

The invention relates, finally, to the use of an above-described kit-of-parts in a method for producing a medical product consisting of a central compartment (3) and an active-ingredient-free overplaster composed of
a) a water vapor-permeable backing layer (1) and
b) a pressure-sensitively adhering, active-ingredient-free polymer layer (2) which is not amine-resistant and which comprises highly water vapor permeable polysiloxanes, polyacrylates without or only with few free acid groups, polyisobutylenes, polybutylenes, styrene-isoprene-styrene block copolymers or styrene-butadiene-styrene block copolymers or the homo- and/or copolymers thereof, wherein the compartment 3 is pressure-sensitively adhering and has direct skin contact after removal of the redetachable protective layer (6), in which an active-ingredient-free overplaster laminated onto an intermediate carrier is adhered, following removal of the intermediate carrier, to a compartment 3.

The particularly preferred embodiments of the present invention below, the drawings, and the working examples serve for further illustration of the invention, without said invention being restricted thereto. Instead, the present invention embraces every combination of (individual) features that is rational to the skilled person, irrespective of whether they are stated in the description, the examples or claims.

In the drawing:

FIG. 1 shows a section through the medical product of the invention.

Figure 2:
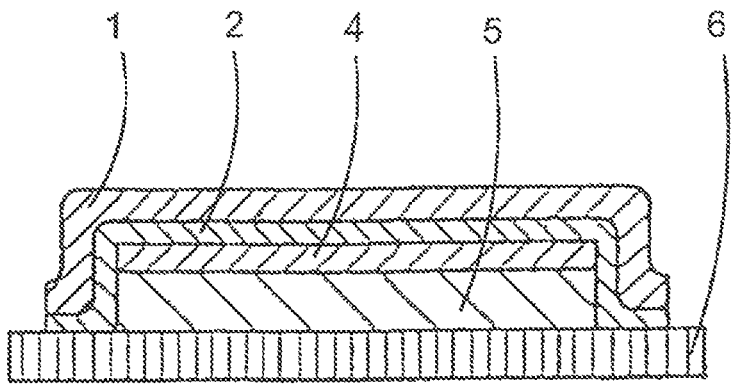
FIG. 2 is a schematic cross-sectional view of a preferred exemplary inventive transdermal therapeutic system.

FIG. 2 shows a section through the preferred TTS of the invention.

In FIGS. 1 and 2 the layer thicknesses have been exaggerated for clarity. In FIG. 1 the pressure-sensitively adhering central compartment (3) is shown schematically with a rectangular cross section. The actual cross section may differ from this.

As can be seen in FIG. 1, compartment 3 rests on the redetachable protective layer (6) and is covered by the overplaster, which is formed from the water vapor-permeable backing layer (1) and the pressure-sensitively adhering, active-ingredient-free polymer layer (2). It can be seen that compartment 3 is overhung on all sides by the backing layer 1 and the polymer layer 2.

As can be seen in FIG. 2, the TTS comprises a pressure-sensitively adhering, active-ingredient-containing polymer layer (5), which rests on the redetachable protective layer (6) and is covered by the overplaster, which is formed from the water vapor-permeable backing layer (1) and the pressure-sensitively adhering, active-ingredient-free polymer layer (2). The separating layer (4) here separates the active-ingredient-containing layer 5 from the pressure-sensitively adhering, active-ingredient-free polymer layer (2). It can be seen that laminate formed from the layers 4 and 5 is overhung on all sides by the backing layer 1 and the polymer layer 2.

In preferred embodiments, the highly skin-compatible, active-ingredient-free polymer layer (2) comprises (percentage quantities indicated here and below are mass fractions [w/w]):
- a "standard PSA" non-amine-resistant polysiloxane adhesive with an optional silicone oil fraction (e.g., silicone oil 12500 cST) for increasing the tack of <4% and a basis weight of <80 g/m$^2$;
- a polyacrylate adhesive without free acid groups, with a neutral oil fraction (e.g., Miglyol) of <5% and a basis weight of <80 g/m$^2$;
- a polyacrylate adhesive without free acid groups, with a dexpanthenol fraction of <5% and a basis weight of <30 g/m$^2$;
- a polyisobutylene-polybutylene adhesive optionally with a neutral oil fraction or silicone oil fraction (e.g., Miglyol or silicone oil 12500 cST) of <5% and a basis weight of <80 g/m$^2$; or
- an adhesive based on styrene-isoprene (alternatively: butadiene)-styrene (SIS) block copolymer (these are often used for increasing the bonding performance with hydrogenated hydrocarbon resins and/or oils such as liquid paraffin in combination. The styrene-isoprene (alternatively to isoprene: butadiene)-styrene block copolymer fraction may amount to between 15-100%, the resin fraction to up to 70%, the oil fraction to up to 50%. The basis weight is <90 g/m$^2$.)

In particularly preferred embodiments, the highly skin-compatible, active-ingredient-free polymer layer (2) comprises:
- a "standard PSA" non-amine-resistant polysiloxane adhesive with an optional silicone oil fraction (e.g., silicone oil 12500 cST) for increasing the tack of ≤1% and a basis weight of ≤70 g/m$^2$;
- a polyacrylate adhesive without free acid groups, with a neutral oil fraction (e.g., Miglyol) of ≤2% and a basis weight of <75 g/m$^2$;
- a polyacrylate adhesive without free acid groups, with a dexpanthenol fraction of ≤2.5% and a basis weight of <75 g/m$^2$;
- a polyisobutylene-polybutylene adhesive optionally with a neutral oil fraction or silicone oil fraction (e.g., Miglyol or silicone oil) of ≤2% and a basis weight of <70 g/m$^2$; or
- an adhesive based on styrene-isoprene (alternatively to isoprene: butadiene)-styrene block copolymer. (These are often used for increasing the bonding performance with hydrogenated hydrocarbon resins and/or oils such as liquid paraffin in combination. The styrene-isoprene (alternatively to isoprene; butadiene)-styrene block copolymer fraction may amount to between 25-100%, the resin fraction to up to 55%, the oil fraction to up to 38%. The basis weight is <75 g/m$^2$.)

The separation layer (4) between active ingredient delivery unit 5 and the overplaster formed from layers 1 and 2 consists preferably of polyethylene terephthalate (PET) with a thickness of 19-23 μm. Where polysiloxane adhesives are utilized in layers 2 or 5, this layer (4) may be siliconized.

Production Examples:

Examples 1-5a (DoE1) with Polyacrylate Adhesive+Neutral Oil:

Preparation of the Composition for the Active-Ingredient-Free Overplaster with Polyacrylate Adhesive Neutral Oil:

A vinyl acetate-acrylate copolymer solution in ethyl acetate/ethanol/heptane with a solids fraction of 40-43% [w/w] is admixed with a solution of neutral oil (Miglyol), and the total solids fraction of the solution is adjusted with ethanol to 40%.

Stirring then takes place until the solution is homogeneous.

This adhesive solution (composition) is utilized for producing the active-ingredient-free, skin-facing side (layer 2) of the overplaster.

Coating and Drying the Composition on Intermediate Carriers:

The composition is coated onto a siliconized PE paper in such a way that, following evaporation of the solvents in a drying cabinet or drying tunnel at not more than 100° C., a layer of adhesive is formed which has a basis weight of 50-100 g/m$^2$.

The compositions of the adhesive solutions used for the overplaster per formulation which follows in the DoE1 (Design of Experiment) trials were:

TABLE 1

| Example | Vinyl acetate-acrylate copolymer solution 42.1% (e.g., DURO-TAK® 387-2515) [g] | Neutral oil MIGLYOL® 812) [g] | Ethanol [g] | Coating weight after drying at about 10-12 min at 60° C. [g/m2] |
| --- | --- | --- | --- | --- |
| Example 1 | 181.6 | 1.6 | 11.9 | 81.1 |
| Example 2 | 368.5 | 0.82 | 30.6 | 52.5 |

TABLE 1-continued

| Example | Vinyl acetate-acrylate copolymer solution 42.1% (e.g., DURO-TAK® 387-2515) [g] | Neutral oil MIGLYOL® 812) [g] | Ethanol [g] | Coating weight after drying at about 10-12 min at 60° C. [g/m2] |
|---|---|---|---|---|
| Example 3 | 368.5 | 0.82 | 30.6 | 114.4 |
| Example 4 | 352.2 | 7.8 | 30.2 | 49 |
| Example 5 | 352.2 | 7.8 | 30.2 | 114.1 |
| Example 5a | 181.6 | 0.8 | 11.9 | 75 |

Examples 6-10 (DoE2) with Polyacrylate Adhesive Dexpanthenol:

Preparation of the Composition for the Active-Ingredient Free Overplaster with Polyacrylate Adhesive+Dexpanthenol:

A vinyl acetate-acrylate copolymer solution in ethyl acetate/ethanol/heptane with a solids fraction of 40-43% [w/w] is admixed with dexpanthenol, and the total solids fraction of the solid is adjusted with ethanol to 40%.

Stirring then takes place until the solution is homogeneous.

This adhesive solution (composition) is utilized for producing the active-ingredient-free, skin-facing side (layer 2) of the overplaster.

Coating and Drying the Composition on Intermediate Carriers:

The composition is coated onto a siliconized PE paper in such a way that, following evaporation of the solvents in a drying cabinet or drying tunnel at not more than 100° C., a layer of adhesive is formed which has a basis weight of 50-110 g/m².

The compositions of the adhesive solutions used for the overplaster per formulation which follows in the DoE2 (Design of Experiment) trials (examples 6-10) were:

TABLE 2

| Example | Vinyl acetate-acrylate copolymer solution 42.1% (e.g., DURO-TAK® 387-2515) [g] | Dexpanthenol [g] | Ethanol [g] | Coating weight after drying at about 10-12 min at 60° C. [g/m2] |
|---|---|---|---|---|
| Example 6 | 180.4 | 2.1 | 12.5 | 80.7 |
| Example 7 | 368.8 | 0.8 | 20.5 | 47.8 |
| Example 8 | 368.8 | 0.8 | 20.5 | 119.2 |
| Example 9 | 352.9 | 7.9 | 30.2 | 50.6 |
| Example 10 | 352.9 | 7.9 | 30.2 | 113.5 |

Examples 11-15 (DoE3) and 16-20 (DoE4) with Non-Amine-Resistant Polysiloxane Adhesive+Silicone Oil:

Preparation of the Composition for the Active-Ingredient-Free Overplaster with Non-Amine-Resistant Polysiloxane Adhesive+Silicone Oil:

A non-amine-resistant polysiloxane adhesive solution in heptane (alternatively ethyl acetate) with a solids content of 50-70% [w/w] is admixed with silicone oil, optionally diluted to 60-70% with n-heptane (or with ethyl acetate in the case of non-amine-resistant polysiloxane adhesives in solution in ethyl acetate), and then stirred until a homogeneous solution is formed. This adhesive solution (composition) is utilized for producing the active-ingredient-free, skin-facing side (layer 2) of the overplaster.

Coating and Drying the Composition on Intermediate Carriers:

The composition is to a fluoropolymer-coated PET film (protective layer and/or intermediate carrier) in such a way that, after evaporation of the solvents in a drying cabinet or drying tunnel at not more than 100° C., a layer of adhesive having a basis weight of 50-80 g/m² is formed.

The compositions of the adhesive solutions used for the overplaster per formulation which follows in the DoE3 (Design of Experiment) trials were:

TABLE 3

| Example | Non-amine-resistant polysiloxane adhesive solution at 60% (e.g., BIO-PSA® 7-4501) [g] | Silicone oil [g] | n-heptane [g] | Coating weight after drying at about 10 min at 50° C. [g/m2] |
|---|---|---|---|---|
| Example 11 | 313.1 | 1.0 | 0.6 | 54.4 |
| Example 12 | 323.1 | 1.0 | 0.6 | 85.9 |
| Example 13 | 310.9 | 7.9 | 5.2 | 51.9 |
| Example 14 | 310.9 | 7.9 | 5.2 | 81.6 |
| Example 15 | 160.5 | 1.0 | 0.7 | 65.9 |

The compositions of the adhesive solutions used for the overplaster per formulation which follows in the DoE4 (Design of Experiment) trials were:

TABLE 4

| Example | Non-amine-resistant polysiloxane adhesive solution at 61% (e.g., BIO-PSA® 7-4601) [g] (possibly different solids content) | Silicone oil [g] | n-heptane [g] | Coating weight after drying at about 10 min at 50° C. [g/m2] (viscosity of the coating composition in dPas) |
|---|---|---|---|---|
| Example 16 | 311.5 | 1.0 | 3.0 | 59.5 |
| Example 17 | 311.5 | 1.0 | 3.0 | 85.8 |
| Example 18 | 306.4 | 7.9 | 10.2 | 59.2 |
| Example 19 | 306.4 | 7.9 | 10.2 | 84.2 |
| Example 20 | 167.4 | 1.0 | 3.4 | 72.6 |
| Example 21 | 160.5 (60%) | 0.7 | 0.7 | 69 (5 dPas) |
| Example 22 | 160.5 (65%) | 0.7 | 0.7 | 70 (8 dPas) |
| Example 23 | 160.5 (67%) | 0.7 | 0.7 | 70 (9.5 dPas) |
| Example 24 | 160.5 (69%) | 0.7 | 0.7 | 70 (15 dPas) |

The dried adhesive surface is lined elastically with a water vapor-permeable backing layer 1, e.g. polyester fabric. This is, for example, a bidirectionally elastic polyethylene-terephthalate fabric which can be stretched in warp and weft directions and whose stretchability is about 50% in lengthwise direction, ≥35% in transverse direction (measured according to DIN 61632), and whose basis weight is about 130 g/m² (manufacturer: Karl Otto Braun GmbH & Co. KG (KOB)).

From the resultant laminates, consisting of intermediate carrier, dry polymer layer 2, and backing layer 1, overplasters of suitable size are then punched out, in order for these to be adhered to the separating layer 4 in the case, for example, of use in combination with an active ingredient delivery layer 5. The punching of the overplaster laminate takes place in such a way that all of the layers are severed apart from the intermediate carrier. The size of the overplaster in comparison to the active ingredient delivery unit, including the separating layer, is a critical determinant here of the size of the overlapping edge region which allows fixing in direct skin contact. The width of the overlapping edge region ought not to be less than 0.4 cm, in order to ensure adequate fixing over 7 days.

Storage Tests

In order to produce a TTS for the storage tests, a vinyl acetate-acrylate copolymer matrix, with a size of 16 cm² and a thickness of 0.1 mm, containing 3.2 mg of estradiol-hemihydrate and 11.2 mg of norethisterol, was lined with an overplaster protruding on all sides, this overplaster being composed of acylate adhesive and bidirectionally elastic PES fabric. The plasters thus produced were packaged in SURLYN® or PET/AL/PAN (BAREX®) sealed edge pouches.

The packaged plasters were then stored for 1.5, 3, 4.5 or 6 months at 40° C. and standard atmospheric humidity or at 40° C. and increased atmospheric humidity. They were subsequently removed from the sealed edge pouches. Assessments were made of the sticking to the pouch material and of the cold flow. In addition, the plasters were investigated by microscope for crystals.

Results and Discussion

TABLE 5

| | 40° C. SURLYN® pouch | 40° C. BAREX® pouch | 40° C. and increased humidity SURLYN® pouch | 40° C. and increased humidity BAREX® pouch |
|---|---|---|---|---|
| 0 mon. | no crystals visible | no crystals visible | no crystals visible | no crystals visible |
| 1.5 mon. (n = 3) | easily removable; no crystals visible | easily removable; no crystals visible | easily removable; no crystals visible | easily removable; no crystals visible |
| 3 mon. (n = 3) | easily removable; no crystals visible | easily removable; no crystals visible | easily removable; no crystals visible | easily removable; no crystals visible |
| 4.5 mon. (n = 3) | easily removable; no crystals visible | easily removable; no crystals visible | easily removable; no crystals visible | easily removable; no crystals visible |
| 6 mon. (n = 6) | easily removable; in one of the six pouches, one round crystal was visible | easily removable; no crystals visible | easily removable; no crystals visible | easily removable; no crystals visible |

Conclusion:

1. By means of the overplaster, the cold flow can be stopped successfully.

2. The crystallization of the active ingredients can be largely prevented by the overplaster. After 6 months at 40° C. and standard atmospheric humidity, a crystal was found only in one case after 6 months. In plasters stored at 40° C. and increased atmospheric humidity, no crystals at all were detectable.

The invention claimed is:

1. A medical product comprising (1) a central compartment and (2) an active-ingredient-free overplaster,
   wherein said medical product is a diagnostic agent, and
   wherein said overplaster comprises
   a) a water vapor-permeable backing layer and
   b) a pressure-sensitive, acting-ingredient-free polymer layer, and
   wherein said central compartment comprises a diagnostic apparatus and is pressure-sensitively adhered to a releasable release liner such that said central compartment can be applied directly to the skin after removal of said releasable release liner,
   said overplaster fixes the central compartment and overhangs said central compartment on all sides and the active-ingredient-free polymer layer comprises non-amine-resistant, highly water vapor-permeable polysiloxanes, polyacrylates or vinyl acetate-acrylate copolymers without free acid groups or with an acid number of less than 1, styrene-isoprene-styrene block copolymers present in combination with at least one of hydrogenated hydrocarbon resins and oils, or styrene-butadiene-styrene block copolymers present in combination with at least one of hydrogenated hydrocarbon resins and oils.

2. A medical product comprising (1) a central compartment and (2) an active-ingredient-free overplaster,
   wherein said medical product is a cannula fixing plaster, and
   wherein said overplaster comprises
   a) a water vapor-permeable backing layer and
   b) a pressure-sensitive, active-ingredient-free polymer layer, and
   wherein said central compartment comprises a cannula and is pressure-sensitively adhered to a releasable release liner such that said central compartment can be applied directly to the skin after removal of said releasable release liner,
   said overplaster fixes the central compartment and overhangs said central compartment on all sides and the active-ingredient-free polymer layer comprises non-amine-resistant, highly water vapor-permeable polysiloxanes, polyacrylates or vinyl acetate-acrylate copolymers without free acid groups or with an acid number of less than 1, styrene-isoprene-styrene block copolymers present in combination with at least one of hydrogenated hydrocarbon resins and oils, or styrene-butadiene-styrene block copolymers present in combination with at least one of hydrogenated hydrocarbon resins and oils.

3. The medical product as claimed in claim 1, wherein the active-ingredient-free polymer layer further comprises a neutral oil as compatibilizer, and the concentration of said neutral oil is 0 to 5% (w/w) based on the layer dry weight.

4. The medical product as claimed in claim 1, wherein the active-ingredient-free polymer layer comprises 0.5 to 5% (w/w) of dexpanthenol, based on the layer dry weight.

5. The medical product as claimed in claim 1, wherein the active-ingredient-free polymer layer comprises non-amine-resistant polysiloxane polymers in which, after polycondensation of a resin fraction and polydimethylsiloxanol groups, remaining silanol groups that are still free have not been capped by methyl groups.

6. The medical product as claimed in claim 1, wherein the active-ingredient-free polymer layer further comprises silicone oil, and the concentration of said silicone oil is 0 to 4% (w/w) based on the layer dry weight.

7. The medical product as claimed in claim 1, wherein the backing layer comprises a bidirectional elastic fabric permeable to water vapor.

8. The medical product as claimed in claim 7, wherein the fabric is a polyester fabric.

9. The medical product as claimed in claim 1, wherein the styrene-isoprene-styrene (SIS) block copolymer or the styrene-butadiene-styrene (SBS) block copolymer is selected as a polymer in the active-ingredient-free polymer layer, and wherein the SIS block polymer or the SBS block copolymer is present in combination with the following oil: liquid paraffin.

10. The medical product as claimed in claim 2, wherein the active-ingredient- free polymer layer further comprises a neutral oil as compatibilizer, and the concentration of said neutral oil is 0 to 5% (w/w) based on the layer dry weight.

11. The medical product as claimed in claim 2, wherein the active-ingredient-free polymer layer comprises 0.5 to 5% (w/w) of dexpanthenol, based on the layer dry weight.

12. The medical product as claimed in claim 2, wherein the active-ingredient-free polymer layer further comprises silicone oil, and the concentration of said silicone oil is 0 to 4% (w/w) based on the layer dry weight.

13. The medical product as claimed in claim 2, wherein the backing layer comprises a bidirectional elastic fabric permeable to water vapor.

14. The medical product as claimed in claim 13, wherein the fabric is a polyester fabric.

15. The medical product as claimed in claim 2, wherein the styrene-isoprene-styrene (SIS) block copolymer or the styrene-butadiene-styrene (SBS) block copolymer is selected as a polymer in the active-ingredient-free polymer layer, and wherein the SIS block polymer or the SBS block copolymer is present in combination with the following oil: liquid paraffin.

\* \* \* \* \*